(12) United States Patent
DJang

(10) Patent No.: US 6,168,795 B1
(45) Date of Patent: Jan. 2, 2001

(54) METHOD FOR ANTICANCER THERAPY USING AN HERBAL EXTRACT COMPOSITION

(75) Inventor: Arthur H. K. DJang, Jamestown, NY (US)

(73) Assignee: Santé International Inc., Jamestown, NY (US)

(*) Notice: Under 35 U.S.C. 154(b), the term of this patent shall be extended for 0 days.

(21) Appl. No.: 09/327,026

(22) Filed: Jun. 7, 1999

Related U.S. Application Data

(60) Provisional application No. 60/088,595, filed on Jun. 9, 1998.

(51) Int. Cl.$^7$ .................................................. A61K 35/78
(52) U.S. Cl. ........................................................ 424/195.1
(58) Field of Search ........................................... 424/195.1

(56) References Cited

U.S. PATENT DOCUMENTS

| | | | |
|---|---|---|---|
| 4,460,488 | * 7/1984 | Grollier et al. | 426/330.3 |
| 4,698,360 | * 7/1984 | Masquelier | 514/456 |
| 4,753,805 | * 6/1988 | Cherukuri et al. | 426/5 |
| 4,935,256 | * 6/1990 | Tsai | 510/119 |

FOREIGN PATENT DOCUMENTS

| | | |
|---|---|---|
| 85105783 | * 1/1987 | (CN) . |
| 1079880 | * 12/1993 | (CN) . |
| 1084703 | * 4/1994 | (CN) . |
| 1100269 | * 3/1995 | (CN) . |
| 1105522 | * 7/1995 | (CN) . |
| 1125517 | * 7/1996 | (CN) . |
| 358059921 | * 4/1983 | (JP) . |
| 2044547 | * 9/1995 | (RU) . |

OTHER PUBLICATIONS

Ahn et al. Planta Med. vol. 64 (5), pp. 468–470, abstract enclosed, May 1998.*

Paschka et al., "Induction of apoptosis in prostate cancer cell lines by the green tea component, (–)epigallocatechin–3–gallate", Aug. 14, 1998, Cancer Letters, vol. 130, pp. 1–7.

* cited by examiner

*Primary Examiner*—Christopher Tate
(74) *Attorney, Agent, or Firm*—M. Bud Nelson

(57) ABSTRACT

Provided is a method of anticancer therapy comprising administering to an individual an herbal extract-based composition comprising an extract of *Gynostemma pentaphyllum,* an extract of *Crataegus pinnatifida* (hawthorn leaves or berries), and an extract of *Camellia sinensis* (green tea). In one embodiment, the anticancer therapy comprises administering to a tumor bearing individual a therapeutically effective amount of the composition. In a second embodiment, the anticancer therapy comprises administering to an individual, at risk of developing a tumor, a prophylactically effective amount of the composition.

12 Claims, 3 Drawing Sheets

METHOD FOR ANTICANCER THERAPY USING AN HERBAL EXTRACT COMPOSITION

This is a nonprovisional application which claims priority to provisional application Ser. No. 60/088,595 filed Jun. 9, 1998, which is herein incorporated by reference.

FIELD OF THE INVENTION

The present invention relates to a method of using an herbal extract-based composition in therapy against tumors. More particularly, provided is a method of anticancer therapy comprising administering either a therapeutically effective amount, or a prophylactically effective amount, of a composition comprising an extract of *Gynostemma pentaphyllum*, an extract of *Crataegus pinnatifida*, and an extract of *Camellia sinensis*.

BACKGROUND OF THE INVENTION

Any one individual is at risk of developing cancer. The occurrence of cancer increases with aging over a life time ("lifetime risk"). For example, in the U.S., men have a 1 in 2 lifetime risk of developing cancer, and women have a 1 in 3 risk. Other risk factors are believed to include genetics, diet, and environmental exposure (e.g., to mutagenic chemicals, radiation, transforming viruses, etc.). It is estimated by the World Health Organization that about 10 million new cancer cases are occurring now annually around the world. That number is expected to reach 15 million by the year 2015, with two thirds of these new cases occurring in developing countries (*World Health* 48:22, 1995). For example, it is estimated that there is about 600,000 new cases of lung cancer per year worldwide; approaching 1 million new cases of breast cancer per year; and for head and neck cancer (the sixth most frequently occurring cancer worldwide) an incidence of 500,000 new cases annually. The National Cancer Institute estimates the overall annual costs for cancer at $107 billion. Treatment costs account for approximately $40 billion.

While new therapeutics are being developed and tested for efficacy against tumors, many of the currently available cancer treatments are relatively ineffective. It has been reported that chemotherapy results in a durable response in only 4% of treated patients, and substantially prolongs the life of only an additional 3% of patients with advanced cancer (Smith et al., 1993, *J. Natl. Cancer Inst.* 85:1460–1474). Many of the current anticancer drugs are both cost-prohibitive, and present with major toxicity. Regarding the latter and depending on the drug or drug combination used, systemic chemotherapy may result in one or more toxicities including hematologic, vascular, neural, gastrointestinal, renal, pulmonary, otologic, and lethal. For example, tamoxifen has been used in women for 25 years to limit breast cancer recurrence. A trial launched in 1992 has shown that tamoxifen is not only effective as a therapeutic agent, but also has a very substantial benefit in cancer prevention (a breast cancer preventative agent). However, in that study, tamoxifen use was shown to have adverse effects in healthy women; i.e., an increased risk of developing uterine cancer or pulmonary blood clots (*Science News*, 1998, 153:228).

Hence, a need still exists for a relatively cost-effective and efficient method for inhibiting growth of tumors, but ameliorate toxicity generally associated with systemic chemotherapy.

SUMMARY OF THE INVENTION

This invention relates to the use of a composition as an anticancer agent for treating cancer in an individual. The composition comprises about 10 to about 30 percent by weight of *Gynostemma pentaphyllum* extract, about 10 to about 30 percent by weight of green tea extract, and about 40 to about 75 percent by weight of hawthorn berries extract. The preferred composition comprising about 10 to about 30 percent by weight of a mixture of an aqueous extract and an alcohol extract of *Gynostemma pentaphyllum*, about 10 to about 30 percent by weight of a mixture of an aqueous extract and an alcohol extract of *Camellia sinensis* (green tea), and about 40 to about 75 percent by weight of a mixture of an aqueous extract and an alcohol extract of *Crataegus pinnatifida* (hawthorn berries). The composition, and a method of making the same is the subject of co-pending and allowed U.S. Pat. No. 5,910,308 (the subject matter of which is herein incorporated by reference) by the present inventor. In one embodiment, this method comprises administering a therapeutically effective amount of the composition to an individual (a mammal; and in a preferred embodiment, a human) bearing a tumor. In another embodiment, the method comprises administering a prophylactically effective amount of the composition to an individual to prevent tumor development (e.g., in an individual who is at high risk for developing tumor; or in an individual who is in remission, but at risk for recurrence).

Thus, a primary object of the present invention is to provide a method for treatment of a tumor bearing individual by administering a therapeutically effective amount of a composition having a property of inhibiting tumor growth when administered to the tumor bearing individual.

Another object of the present invention is to provide a method for prevention of tumor development in an individual at risk for tumor development by administering a prophylactically effective amount of a composition having a property of inhibiting tumor growth when administered to the individual.

Another object of the present invention is to provide a method of treatment of a tumor bearing individual, or an individual at risk for developing tumor, with a therapeutically effective amount of a composition that has both properties of inhibiting tumor growth, and being substantially non-toxic when administered to the individual. "Substantially nontoxic" means that the composition lacks the toxicity generally associated with systemic chemotherapy; i.e., lacks detectable toxicities including hematologic, vascular, neural, gastrointestinal, renal, pulmonary, otologic, and immunosuppression (which may lead to lethal infections).

A further object of the present invention is to provide a method of treatment of an individual who has had a substantial reduction in tumor burden but who still is at risk for recurrence, wherein the method comprises administering to the individual a prophylactically effective amount of a composition that has both properties of inhibiting tumor growth, and being substantially non-toxic when administered to the individual.

The above and other objects, features, and advantages of the present invention will be apparent in the following Detailed Description of the Invention when read in conjunction with the accompanying drawings and embodiments.

DETAILED DESCRIPTION OF THE INVENTION

Figure 1A:
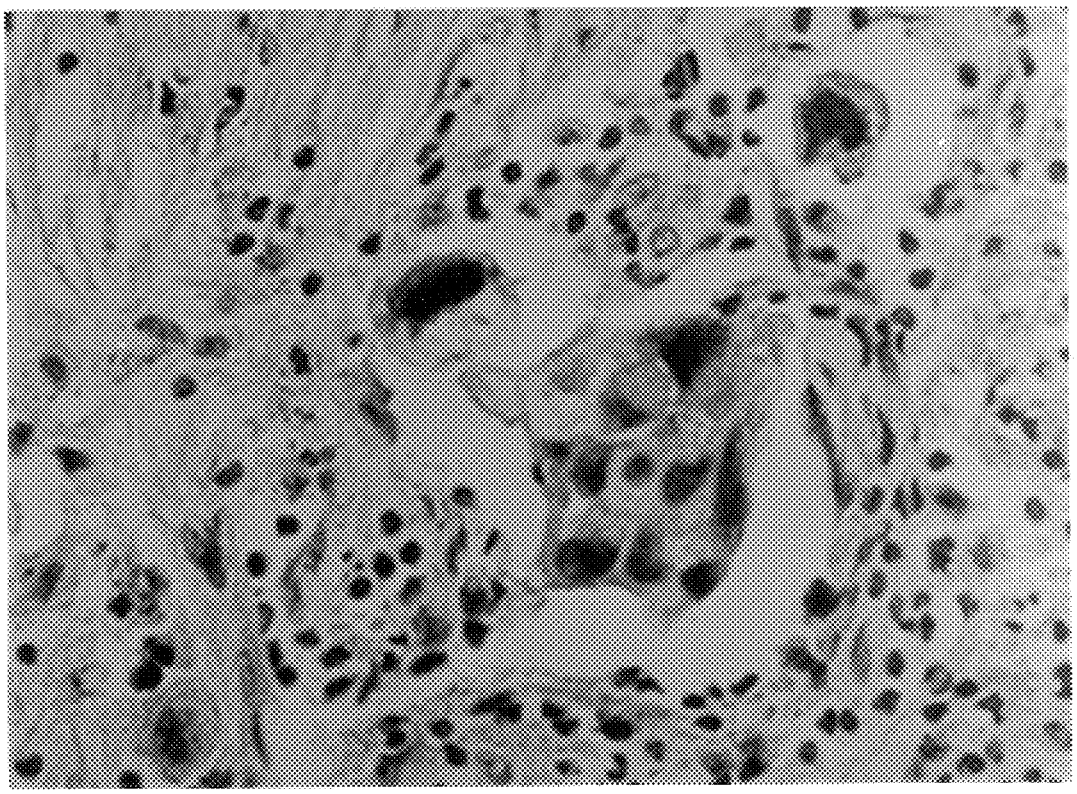
FIG. 1A is a photograph of a histochemical staining of a mounted tissue section of a breast infiltrating ductal carcinoma from a 51 year old woman before anticancer therapy.

The present invention relates to a novel discovery that a herbal extract-based composition can effectively inhibit tumor growth and be substantially nontoxic when administered to an individual. "Tumor" is used herein, for purposes of the specification and claims, to mean solid nonlymphoid primary tumor of ductal epithelial cell origin, including, but not limited to, tumors originating in the breast, prostate, colon, lung, pancreas, liver, stomach, bladder, or reproductive tract (cervix, ovaries, endometrium etc.), brain, and bone marrow; melanoma; or lymphoma. "Inhibiting tumor growth" is used herein, for purposes of the specification and claims, to mean one or more of slowing the growth of the tumor, halting growth of the tumor, causing reduction or regression of the tumor, inhibiting tumor invasion, causing tumor cell death, and causing reduction or regression of metastases. "Prevention of tumor development" is used herein, for purposes of the specification and claims, to mean inhibiting growth of the tumor; and more specifically, causing tumor cell death in preventing tumor mass formation.

The composition

The composition comprises about 10 to about 30 percent by weight of *Gynostemma pentaphyllum* extract, about 10 to about 30 percent by weight of green tea extract, and about 40 to about 75 percent by weight of hawthorn berries extract. *Gynostemma pentaphyllum,* also known as 5-leaf ginseng or Jiaogulan or southern ginseng, is from the cucumber family and has traditionally been grown in a mountainous region in South Central China. This herb, a completely different plant than ginseng, is rich in special saponins termed "gypenosides" which are similar, and some identical, to the ginsenosides found in ginseng, but at a level several fold higher. These saponins have been shown to have antioxidant/cell protective effects. More particularly, the saponins protected cell membranes and cytosols, from oxidative injury, neutralize free radicals, helped preserve immune function during irradiation, lowered blood pressure, reduced vascular resistance, effects anti-platelet-aggregation, and reduced levels of serum triglycerides and total cholesterol (Gormley et al., 1997, *Better Nutrition* 59:42). The leaves and berries of *Crataegus pinnatifida,* also known as hawthorn, have been used traditionally for the treatment of heart conditions and for cardiovascular health. The hawthorn fruits (berries), known as "Shan-zha, have been used to improve digestion, and to alleviate various stomach ailments. Saponins, flavonoids (including hyperoside), and anthocyanins (including proanthocyanidins) extracted form hawthorn fruits have also shown cardiotonic (heart stimulating and regulating) activity including inhibition of arrhythmia, normalization of blood pressure, dilation of blood vessels and increase in coronary blood flow, reduction of serum triglyceride and cholesterol levels, reduction in symptoms of angina, and improvement of circulation (Foster, 1997, *Better Nutrition,* 59:56; Foster, 1989, *Bestways* 17:46; McCaleb, 1991, *Better Nutrition for Today's Living* 53:32). Dried leaves from the *Camellia sinensis* plant is processed into three types of tea: oolong tea, black tea, and green tea. In making green tea, the tea leaves are stabilized by moist or dry heat which destroys the enzyme polyphenoloxidase and thus, prevents oxidation of polyphenols. These polyphenols are the main biologically active ingredients in green tea. Catechins, a chemical group of polyphenols possessing antioxidant properties (protects cells from free radical-mediated damage), include epigallocatechin-3 gallate (ECGC), epigallocatechin, and epicatechin-3-gallate. Recently, ECGC has been shown to be an inhibitor of urokinase (Jankun et al., 1997, *Nature* 387:561), and quinoloxidase; enzymes that may be crucial for growth of tumor cells. While *Gynostemma pentaphyllum, Crataegus pinnatifida,* and *Camellia sinensis* have been used individually for health promoting and therapeutic purposes, not described is a human tumor inhibiting property, nor a tumor inhibiting property conferred by a composition comprising an extract of *Gynostemma pentaphyllum,* an extract of *Crataegus pinnatifida* (hawthorn berries or leaves) and an extract of *Camellia sinensis* (green tea). It is believed that the tumor inhibiting properties observed for the composition used in the method according to the present invention are a result of a novel combination of components comprising the saponins present in the extract of *Gynostemma pentaphyllum,* one or more of saponins and flavonoids and polyphenols present in the extract of *Crataegus pinnatifida,* and the polyphenols present in the extract of *Camellia sinensis.*

It is noted that plants are considered a valuable resource for the discovery and development of novel, naturally derived agents to treat cancer. In that regard, six plant-derived anticancer agents have received FDA approval (e.g., taxol, vinblastine, vincristine, topotecan, etoposide, teniposide), with other agents being evaluated in clinical trials (e.g., camptothecin, 9AC, and irinotecan).

Mouse models for human disease

In some of the following embodiments used to illustrate the methods of the present invention, it is important to consider the following concept. A mouse subrenal capsule assay utilizing a human xenograft was utilized to determine antitumor activity. The well-vascularized subrenal capsule site has been described as an excellent model that simulates clinical tumor microenvironment (Bogden et al., 1981, *Cancer* 48:10–20; Donaldson et al., 1990, *Urol. Res.* 18:245–250). The human xenograft is a tumor fragment that retains cell membrane integrity, cell-to-cell contact, and spatial relationship of the heterologous cell populations; thereby providing intact permeability barriers necessary for testing of new antitumor agents, and permitting determination of net response to treatment with the agent by direct measurement of tumor xenograft size (Cobb et al., 1983, *Cancer Treat. Rep.* 67:173–8).

Further, the subrenal capsule assay may be used to determine the toxicity to a host associated with administration of an anticancer agent (Donaldson et al., 1990, supra). The subrenal capsule assay utilizing a human xenograft has been used to determine antitumor activity against human tumors which include, but are not limited to: renal cell carcinoma (Donaldson et al., 1990, supra; Iwagaki et al., 1988, *J. Med.* 19:21–31); gastric cancer (Iwagaki et al., 1988, supra; Yamauchi et al., 1991, *J. Surg. Oncol.* 47:98–101; Maehara et al., 1990, *Semin. Surg. Oncol.* 6:42–7); colorectal cancer (Iwagaki et al., 1988, supra; Maehara et al., 1990, supra; Cobb et al., 1983, *Cancer Treat. Rep.* 67:173–8); breast cancer (Iwagaki et al., 1988, supra; Bogden et al., 1981, supra; Cobb et al., 1983, supra); liver cancer (Iwagaki et al., 1988, supra; ; Maehara et al., 1990, supra) ; melanoma (Ryabkova et al., 1994, *Oncology* 51:54–43; Hahka-Kemppinen et al., 1996, *Melanoma Res.* 6:215–21); chorio-carcinoma (Ogino et al., 1990, *Gynecol. Oncol.* 38:32–36); ovarian adenocarcinoma (Stratton et al., 1984, *Gynecol. Oncol.* 18:145–9; Cobb et al., 1983, supra); lung cancer (Cobb et al., 1983, supra; Aamdal et al., 1985, *Anticancer Res.* 5:329–37); cervical cancer (Cobb et al., 1983, supra); eosophageal cancer (Nishiyama et al., 1988, *Jpn. J. Surg.* 18:93–7; Terashima et al., 1990, *Gan. To. Kagaku. Ryoho.* 17:269–73); prostate carcinoma (Murahashi et al., 1988, *Gan. To. Kagaku. Ryoho.* 15:231–5); and urinary bladder carcinoma (Murahashi et al., 1988, supra).

The subrenal capsule assay utilizing a human xenograft has been used to determine antitumor activity of agents including, but not limited to, a combination of human tumor necrosis factor (TNF) and etoposide; mitomycin-C; 5-fluorouracil (5-FU); adriamycin; cisplatin; a combination of TNF and human interferon; hexycarbamyl-5-FU; sarcolysine; melanostatin; methotrexate; tamoxifen; cytoxan; actinomycin D; cyclophosphamide; doxorubicin; vinblastine sulfate; homoharringtonine; tricyclic nucleotide; bleomycin; vincristine; and combinations thereof. The use of the subrenal capsule tumor xenograft assay has been validated as a model that can accurately predict the chemosensitivity of that tumor growing in its autochthonous host (Bennett et al., 1986, *J. Surg. Oncol.* 33:8–13). The use of the subrenal capsule human tumor xenograft assay has also been validated as a model that can accurately evaluate chemotherapeutic agents for efficacy because the model has been shown to reflect the clinical effectiveness of chemotherapeutic agents in human patients treated with these agents and reflects antitumor effects from the agents, such as tumor regression or inhibition of tumor growth, as consistent with the activity against the corresponding types of clinical cancer (Yamauchi et al., 1991, supra; Bogden et al.. 1981, supra; Hahka-Kemppinen et al., 1996, supra). In that regard, the subrenal capsular assay using human xenografts has been reported to have high predicitivity, ranging from at least 77% to 80%, of chemosensitivity in clinical situations (Terashima, 1987, *Nippon Geka Gakkai Zasshi*, 88:1554–64; Inoue, 1989, *Gan. No. Rinsho.* 35:1535–40). The Tianjin Cancer Institute and Hospital, the clinical research/experimental pathology laboratory where the subrenal capsule assay with human tumor xenografts was performed as a standard animal model for testing the composition in the method according to the present invention, has used this assay for 15 years and have observed a predictivity of clinical effectiveness of 90.7%. Additionally, having evaluated parameters such as clinical efficacy and pharmacokinetics in the appropriate mouse model, the anticancer therapy may then be "scaled up" to human treatment. A physiological basis for scaling up the therapeutic agents from a mouse model to humans is known to those skilled in the art (e.g., the average body weight of a mouse used in this model is approximately 20 grams).

The method of inhibiting tumor growth by administering a therapeutically effective amount of the composition according to the present invention may be more apparent by the following examples which are provided for purposes of illustration, and not limitation.

EXAMPLE 1

In this embodiment, illustrated is a comparison of efficacy in inhibiting different tumor types between the composition for use in the present invention ("LC") with various chemotherapeutic drugs, and combinations thereof, using the subrenal capsule assay with human tumor xenografts.

The subrenal capsule assay with human tumor xenografts was performed as follows. A human breast carcinoma, of the infiltrating ductal variety, was surgically resected and immediately transported to the clinical laboratory in sterile tissue culture medium (RPMI 1640). Upon arrival, a portion of the human tumor explant was used for surgical pathology to confirm neoplastic properties. A portion of the human tumor explant was carefully dissected with scalpels into multiple fragments of 1 $mm^3$ in size. A human tumor explant fragment was implanted under the renal capsule each of several groups of BALB/c mice (8 week old males) using a standard technique known in the art. Briefly, each mouse was anesthesized, an incision was made in the left flank, and the kidney was exteriorized. A shallow incision, about 1 cm long, was made on the convex side of the kidney near the caudal pole. The human tumor explant fragment (one xenograft per mouse) was implanted below the transparent capsule. After implant, the abdominal wall and the skin were closed with sutures. On Day 0, initial body weights of the mice, as well as the initial in situ tumor fragment size, were determined. On Day 1 after implant, anticancer agent and/or chemotherapeutic agents were administered daily, with the dose levels and routes of administration as summarized in Table 1. On Day 5, final body weights were taken, and the tumor bearing kidneys were excised for determining the final in situ tumor size and cellular characteristics. Using a stereoscopic magnifying microscope fitted with an ocular micro-meter, tumor size was measured, wherein 1 mm=10 ocular micrometer units (omu). Tumor size is expressed as an average of the length and width: (L+W)/2. At Day 5, also analyzed by microscopy were any morphological and cellular changes in the tumor, including karyopyknosis, karyorrhexis, eosinophilic degeneration of cytoplasm, and necrosis with lymphocytic and polymorphonuclear leucocytic infiltration. As illustrated in Table 1, tamoxifen ("TMF"), and a combination cyclophosphamide-methotrexate-5-FU ("CMF"), were used separately or in combination with LC.

TABLE 1

| Agent | Dose/day | Route |
| --- | --- | --- |
| Control (placebo) | | |
| CMF | C: 50 mg/kg; M: 4 mg/kg; F: 50 mg/kg/day | subcutaneous (SC) |
| LC (L) | 50 mg/mouse/day | gastric tube (GT) |
| LC (M) | 100 mg/mouse/day | GT |
| LC (H) | 200 mg/mouse/day | GT |
| CMF + LC (L) | see above | see above |
| CMF + LC (M) | see above | see above |
| CMF + LC (H) | see above | see above |
| TMF | 0.16 mg/mouse/day | GT |
| TMF + LC (M) | see above | see above |
| TMF + CMF | see above | see above |

The activity of the agent to inhibit tumor growth is measured as a change in tumor size ($\Delta TS$) between Day 0 ($TS_0$) and Day 5 ($TS_5$) by the formula: $\Delta TS=(TS_5-TS_0)$. An agent causing a reduction in relative tumor size of greater than 0.5 omu ($\Delta TS<-0.05$) is considered an agent with efficacy in inhibiting tumor growth. Illustrated in Table 2 is a comparison of the mean results (5 mice per treatment agent) on tumor growth by treatment with CMF versus CMF+LC versus LC, using the subrenal capsule assay with human breast infiltrating ductal carcinoma xenografts.

TABLE 2

| Agent | $TS_0$ | $TS_5$ | ΔTS |
|---|---|---|---|
| CMF | 11.35 | 11.3 | −0.05 |
| CMF + LC (L) | 11.8 | 11.0 | −0.08 |
| CMF + LC (M) | 12.6 | 9.7 | −2.9 |
| CMF + LC (H) | 13.35 | 11.2 | −2.15 |
| LC (L) | 12.0 | 10.5 | −1.5 |
| LC (M) | 13.95 | 12.55 | −1.4 |
| LC (H) | 11.9 | 9.95 | −1.95 |
| Control | 12.0 | 12.5 | +0.5 |
| TMF | 11.44 | 9.38 | −2.06 |
| CMF + TMF | 13.4 | 12.0 | −1.4 |
| TMF + LC (M) | 13.8 | 10.45 | −3.35 |
| TMF + LC (H) | 12.56 | 11.06 | −1.5 |

Illustrated in Table 3 is a comparison of the mean results (5 mice per treatment agent) on tumor growth by treatment with CFMF versus CFMF+LC versus LC, using the subrenal capsule assay with human colorectal adenocarcinoma xenografts. LC (M) comprises 100 mg, and LC (H) comprises 150 mg. CF is citrovorum factor administered subcutaneously at 0.4 mg/kg/day. M is methotrexate and F is 5-FU as outlined above.

TABLE 3

| Agent | $TS_0$ | $TS_5$ | ΔTS |
|---|---|---|---|
| CFMF | 16.4 | 13.6 | −2.8 |
| CFMF + LC (M) | 15.3 | 12.2 | −3.1 |
| CFMF + LC (H) | 20.8 | 14.8 | −6.0 |
| LC (M) | 18.55 | 16.5 | −1.95 |
| LC (H) | 17.9 | 17.3 | −0.6 |
| Control | 17.83 | 19.33 | +1.5 |

Illustrated in Table 4 is a comparison of the mean results (5 mice per treatment agent) on tumor growth by treatment with CAD versus CAD+LC versus LC, using the subrenal capsule assay with human lung squamous cell carcinoma xenografts. LC (M) comprises 100 mg, and LC (H) comprises 150 mg. C is cytoxan, administered subcutaneously at 10 mg/kg/day; A is adriamycin, administered subcutaneously at 1.6 mg/kg/day; and D is cisplatin administered subcutaneously at 1.6 mg/kg/day.

TABLE 4

| Agent | $TS_0$ | $TS_5$ | ΔTS |
|---|---|---|---|
| CAD | 14.81 | 12.25 | −2.56 |
| CAD + LC (M) | 15.25 | 12.11 | −3.63 |
| CAD + LC (H) | 17.93 | 10.94 | −6.99 |
| LC (M) | 15.37 | 15.31 | −0.06 |
| LC (H) | 17.75 | 17.75 | 0 |
| Control | 16.29 | 17.08 | +0.79 |

From the results of this assay, and similar assays using two additional human tumor xenografts, several conclusions can be drawn. First, note that the control group of mice receiving a placebo showed a positive ΔTS. A positive ΔTS in a placebo or untreated group is a quality control factor reflective of not only the quality of tissue preparation implanted for the assay, but also the growth potential of the human tumor implanted as a test indicator. Secondly, and in treatment of human mammary ductal carcinoma xenografts, while a standard combination of chemotherapy drugs cyclophosphamide/methotrexate/5-FU showed efficacy in inhibiting human tumor growth, all doses of the composition, LC, tested in this assay showed greater ability to inhibit human tumor growth. Further, LC (H) appears to have an approximately equivalent ability to inhibit tumor growth as does tamoxifen, a known preventative and therapeutic agent for human anticancer therapy. However, in contrast to tamoxifen, in human usage to date, LC has shown no adverse side effects.

Additionally, when chemotherapeutic drug combinations were combined with LC (LC daily dose at either the M dose or H dose), observed was a synergistic effect. A synergistic effect means that the combination showed greater efficacy in inhibiting tumor growth than expected. For example, LC (M) had a mean ΔTS of −1.4, and CMF had a mean ΔTS of −0.05. Thus, a combination of LC (M)+CMF would be expected to result in a mean ΔTS of −1.9. However, the combination of LC (M)+CFMF resulted in a mean ΔTS of −2.9 which is significantly greater tumor inhibition than a mean ΔTS of −1.9; and hence, represents a synergistic effect. In another example, LC (H) had a mean ΔTS of −0.6, and CFMF had a mean ΔTS of −2.8. Thus, a combination of LC (H)+CFMF would be expected to result in a mean ΔTS of −3.4. However, the combination of LC (H)+CFMF resulted in a mean ΔTS of −6.0 which is significantly greater tumor inhibition than a mean ΔTS of −3.4; and hence, represents a synergistic effect. In yet another example, LC (H) had a mean ΔTS of 0, and CAD had a mean ΔTS of −2.56. Thus, a combination of LC (H)+CAD would be expected to result in a mean ΔTS of −2.56. However, the combination of LC (H)+CAD resulted in a mean ΔTS of −6.99 which is significantly greater tumor inhibition than a mean ΔTS of −2.56; and hence, represents a synergistic effect. It is of significance that LC acts synergistically in combination with chemotherapeutic drugs in inhibiting tumor growth and may additionally cause tumor regression. Taken together, these results suggest that LC may act to inhibit one or more mechanisms involved in tumor growth common to many tumor types. It is also noted that chemotherapeutic drugs like cisplatin, adriamycin, cytoxan, 5-FU, and methotrexate are believed to act by mechanisms that interfere with DNA synthesis which is essential to cell division and growth. From the data to date, it appears that LC acts by mechanisms other than interfering with DNA synthesis, hence the ability of LC to complement and act synergistically with chemotherapeutic agents that interfere DNA synthesis.

Figure 1B:
FIG. 1B is a photograph of a histochemical staining of a mounted tissue section of the same explant as shown in FIG. 1A but after xenografting into a mouse, and after treatment with the method according to the present invention.
Figure 2A:
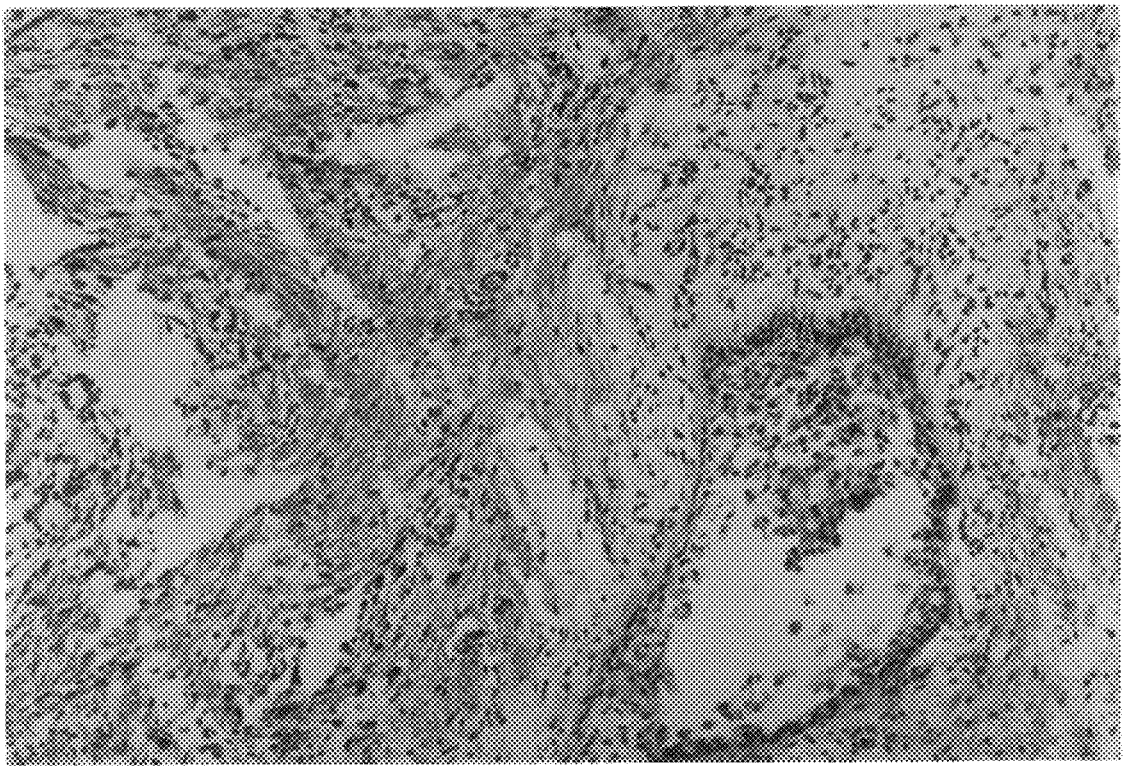
FIG. 2A is a photograph of a histochemical staining of a mounted tissue section of a breast infiltrating ductal carcinoma from a 47 year old woman before anticancer therapy.
Figure 2B:
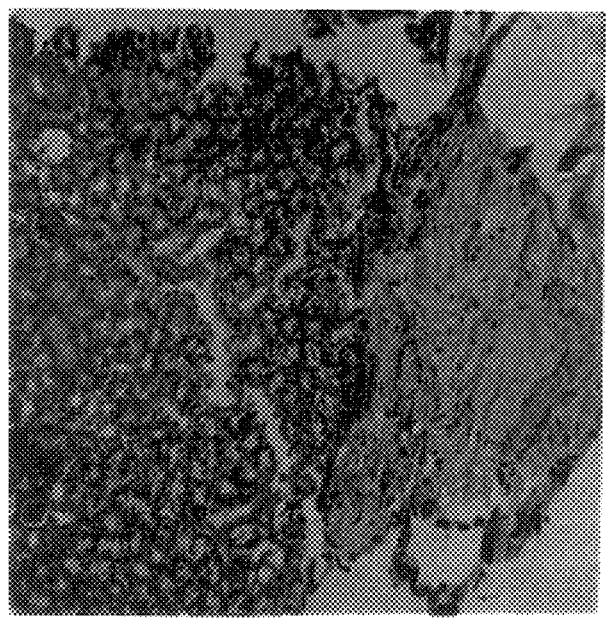
FIG. 2B is a photograph of a histochemical staining of a mounted tissue section of the same explant as shown in FIG. 2A but after xenografting into a mouse, and after treatment with the method according to the present invention.
Figure 3A:
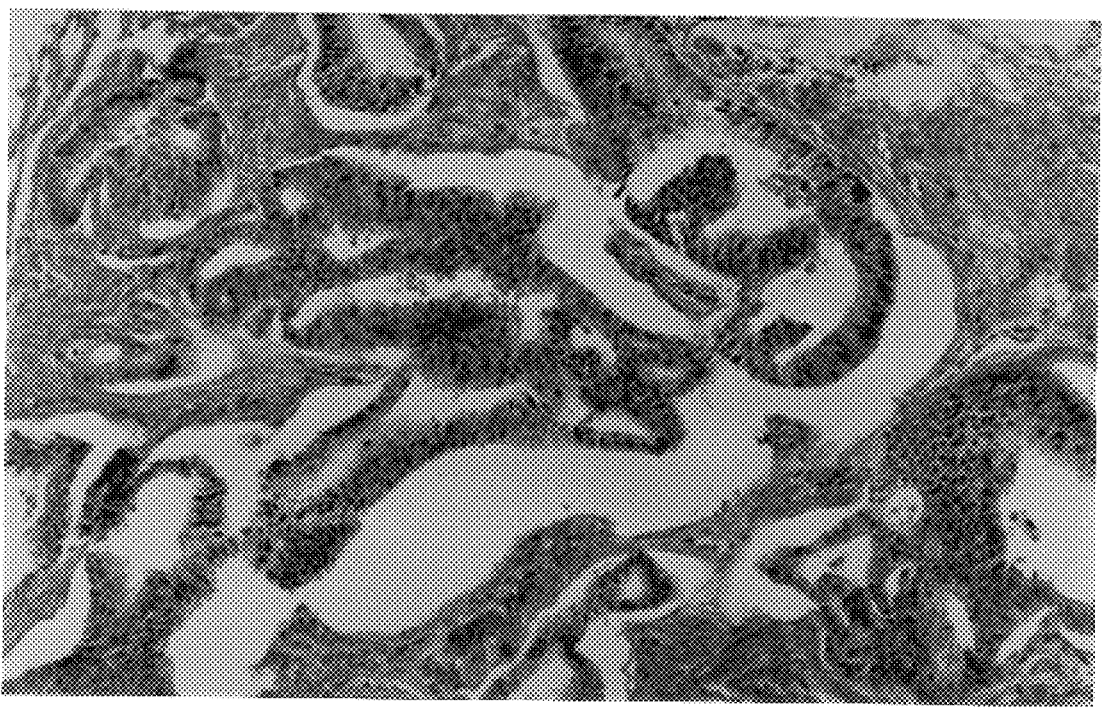
FIG. 3A is a photograph of a histochemical staining of a mounted tissue section of a breast infiltrating ductal carcinoma from a 60 year old woman before anticancer therapy.

Illustrated are three different human xenografts used as explants in the subrenal capsule assay. FIG. 1A is a photograph of a histochemical staining of a mounted tissue section of a breast infiltrating ductal carcinoma from a 51 year old woman before anticancer therapy; whereas FIG. 1B shows the xenograft after anticancer therapy with LC (M) in the subrenal capsule assay. Note in FIG. 1B, as contrasted with FIG. 1A, that the treated shows disappearance of most tumor cells, and interstitial hyalinization. The remaining tumor cells show shrinkage, karyopyknosis and karyorrhexis. There is no apparent invasion into the adjacent renal parenchyma. FIG. 2A is a photograph of a histochemical staining of a mounted tissue section of a breast infiltrating ductal carcinoma from a 47 year old woman before anticancer therapy; whereas FIG. 2B shows the xenograft after anticancer therapy with LC (H) in the subrenal capsule assay. Note in FIG. 2B, in contrast to FIG. 2A, the xenograft shows stromal hyalinization, shrinkage of tumor, and disappearance of most tumor cells. The remaining tumor cells show karyopyknosis and karyorrhexis. There is no apparent invasion into the adjacent renal parenchyma. FIG. 3A is a photograph of a histochemical staining of a mounted tissue section of a breast infiltrating ductal carcinoma from a 60 year old woman before anticancer therapy; whereas FIG. 3B shows the xenograft after anticancer therapy with LC (L) in the subrenal capsule assay.

Figure 3B:
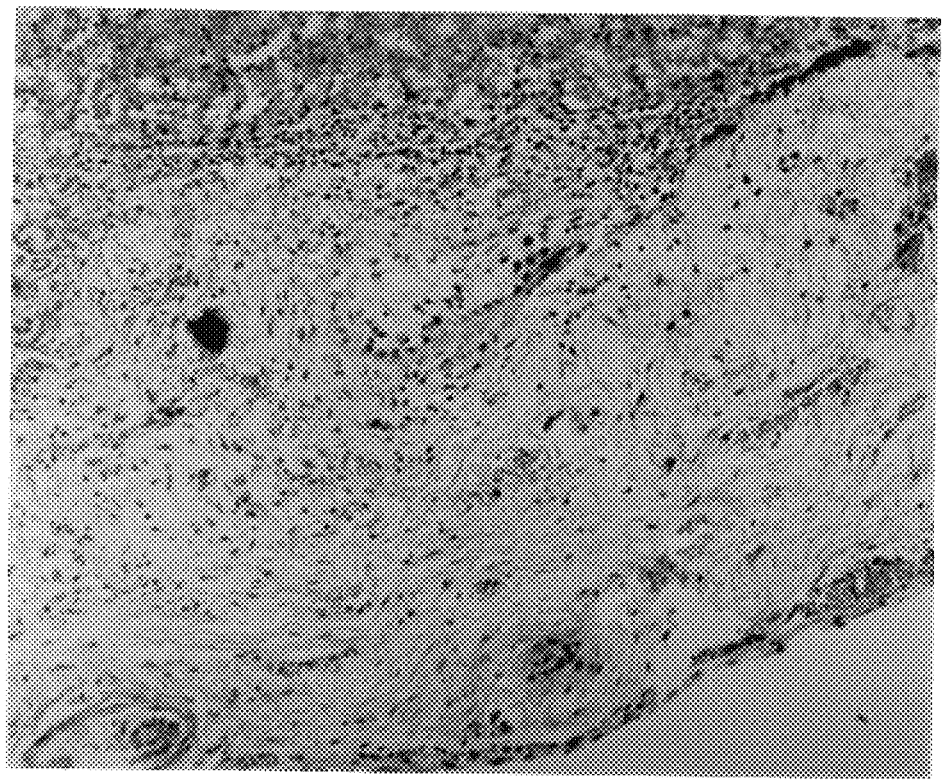
FIG. 3B is a photograph of a histochemical staining of a mounted tissue section of the same explant as shown in FIG. 3A but after xenografting into a mouse, and after treatment with the method according to the present invention.

Note in FIG. 3B, in contrast to FIG. 3A, the treated xenograft shows a substantial reduction in the number of tumor cells, and interstitial hyalinization. The remaining tumor cells show shrinkage, karyopyknosis and karyorrhexis. The periphery of the tumor xenograft shows lymphocytic and polymorphonuclear leucocytic infiltrates. There is no apparent invasion into the adjacent renal parenchyma.

In summary, these results illustrate that using the method according to the invention for treating an individual, there is regression of human tumors. Regression appeared to be effected by multiple mechanisms including apoptosis of tumor cells, inhibition of angiogenesis of tumors, and reduction of the invasiveness of the tumors. This inhibition of tumor development is noted in a standard animal model for human tumors which, according to the past 15 years of use, has shown greater than 90% concordance with clinical effectiveness of tumor-sensitive chemotherapeutic agents.

EXAMPLE 2

In this example, illustrated are embodiments of a method of according to the present invention for anticancer therapy. In a first embodiment, the anticancer therapy comprises administering to a tumor bearing individual a therapeutically effective amount of the composition, referred herein for purposes of reference as "LC". The composition, LC, comprises about 10 to about 30 percent by weight of *Gynostemma pentaphyllum* extract, about 10 to about 30 percent by weight of green tea extract, and about 40 to about 75 percent by weight of hawthorn berries extract; and is made according to the method described in copending and allowed U.S. patent application Ser. No. 08/905,128 (the disclosure of which is herein incorporated by reference). A therapeutically effective amount is an amount that can effect tumor inhibition when administered to a tumor bearing individual. As known to those skilled in the art, the dosage and regimen may vary with the individual depending on such factors as the age, size, health, and metabolism of the individual; the type of tumor; the stage of tumor progression; and related factors. The route of administration may be by any conventional route in which the composition can be safely and effectively delivered. Typically, anticancer agents can be administered by one or more routes including, but not limited to, intravenously, subcutaneously, orally, intramuscularly, and intradermally. In the method of the present invention, a preferred route of administration is an oral route. The composition may be administered in tablet/caplet/capsule form, or in a liquid form in a pharmaceutically acceptable carrier (e.g., liquid, water, saline or other physiological solution, or gel).

As one illustration of this embodiment, a 34 year old female was diagnosed by radiographic evaluation as having a mammary intraductal papilloma. The individual was administered, by an oral route and in caplet form, 500 mg LC, four to five times per day. After four weeks, radiographic evaluation of the individual showed that the tumor completely regressed to the point it was no longer radiographically detectable. Additionally, sero-sanguinous discharges from the nipple, present before treatment, stopped completely as a result of the treatment. No symptoms of toxicity in the individual were observed during treatment according to the method of the present invention.

In another illustration of this embodiment, a 71 year old male was diagnosed as having prostate carcinoma with bladder wall extension and adjacent lymph node metastases. The individual did not receive previous standard chemotherapy nor radiation therapy. The individual was administered, by an oral route, 750 mg LC, three times per day. After three months of treatment, digital rectal evaluation of the individual showed that the 4 hard nodules observed before treatment were reduced to only one soft palpable nodule. Additionally, the tumor marker prostate-specific antigen (PSA) that was 28 µg/L before treatment, was reduced to 0.7 µg/L as a result of treatment (the normal range soft palpable nodule. Additionally, the tumor marker prostate-specific antigen (PSA) that was 28 µg/L before treatment, was reduced to 0.7 µg/L as a result of treatment (the normal range being <4.1 µg/L). No symptoms of toxicity in the individual were observed during treatment according to the method of the present invention.

In another illustration of this embodiment, a 54 year old female was diagnosed by analyses of bone marrow aspirates and bone scans as having malignant lymphoma of the small cell follicular type, with panmyelosis. The individual's prognosis for survival, given extensive and diffuse bone metastasis, was 2 months. The individual suffered excruciating bone pain in the back and down her left side, for which she took a prescription painkiller (morphine). The individual was unable to walk except with the assistance of crutches. The individual could not tolerate more than a few days of chemotherapy with leukeran. Chemotherapy was stopped, and the individual was administered, by an oral route, 750 mg LC, three times per day. After three months of treatment, radiological evaluation of the individual showed a reduction of the diffuse bone metastasis. In that regard, the individual was able to walk unassisted, and no longer took painkillers as the pain had subsided. No symptoms of toxicity in the individual were observed during treatment according to the method of the present invention.

In another illustration of this embodiment, a 55 year old male was diagnosed as having squamous carcinoma of the lung with left axillary lymph node metastases. The individual did not receive previous standard chemotherapy nor radiation therapy. The individual was administered, by an oral route, 750 mg LC, three times per day. After 6 weeks of treatment, imaging evaluation of the individual showed the reduction of lung infiltrate and that the left axillary lymph nodal mass of 5 cm by 4 cm had been reduced to a mass of 2 cm by 2 cm as a result of treatment. Further follow-up was not possible, as the individual moved out of the country. No symptoms of toxicity in the individual were observed during treatment according to the method of the present invention.

In another illustration of this embodiment, a 49 year old male individual was diagnosed as having metastatic melanoma with a primary tumor on a left finger, with left axillary lymph node and second anterior rib metastases. The primary tumor was surgically excised from the individual, and a subsequent biopsy of the surgical area showed no residual tumor. The individual was administered, by an oral route, 750 mg LC, three times per day. After two months of treatment, imaging evaluation of the individual showed that the lung fields were clear, with an absence of pulmonary nodules, and a disappearance of detectable metastases in the left second anterior rib. No symptoms of toxicity in the individual were observed during treatment according to the method of the present invention.

In an alternative, the method of according to the present invention for anticancer therapy further comprises administering a therapeutically effective amount of one or more standard anticancer treatments (e.g., one or more of radiation therapy, chemotherapy, surgery, immunotherapy, and photodynamic therapy) in addition to administering a therapeutically effective amount of the composition, LC. In a preferred embodiment of this alternative, the method comprises administering a therapeutically effective amount of one or more standard chemotherapeutic drugs in addition to administering a therapeutically effective amount of the composition, LC. As illustrated herein, a combination of a therapeutically effective amount of one or more standard chemotherapeutic drugs and a therapeutically effective amount of the composition, LC, can result in a synergistic effect in tumor inhibition (including regression of existing tumor).

In a second embodiment, the anticancer therapy comprises administering to an individual, at risk of developing a tumor, a prophylactically effective amount of the composition, LC. A prophylactically effective amount is an amount that can effect tumor inhibition when administered to an individual at risk of developing a tumor (new tumor or recurrence). As known to those skilled in the art, the dosage may vary with the individual depending on the age, size, health, and metabolism of the individual, and related factors. The route of administration may be by any conventional route in which the composition can be safely and effectively delivered. A preferred route of administration is an oral route. The composition may be administered in tablet/caplet/capsule form, or in a form in a pharmaceutically acceptable carrier (e.g., liquid, water, saline or other physiological solution, or gel). In an illustration of this embodiment, a 48 year old female was diagnosed by cytological evaluation as having stage II, high grade breast infiltrating ductal carcinoma. The individual underwent segmental mastectomy and right axillary lymph node dissection (with 7 positive nodes out of 19 axillary nodes). The individual was administered, by an oral route, 750 mg LC, three times per day. After seven months, valuation of the individual showed no additional identifiable metastases. No symptoms of toxicity in the individual were observed during treatment according to the method of the present invention.

From the foregoing, it will be obvious to those skilled in the art that various modifications in the above-described methods, and compositions can be made without departing from the spirit and scope of the invention. Accordingly, the invention may be embodied in other specific forms without departing from the spirit or essential characteristics thereof. Present embodiments and examples, therefore, are to be considered in all respects as illustrative and not restrictive, and all changes which come within the meaning and range of equivalency of the claims are therefore intended to be embraced therein.

What is claimed is:

1. A method of anticancer therapy comprising administering to a tumor bearing individual a therapeutically effective amount of a composition comprising about 10 to about 30 percent by weight of a mixture of an aqueous extract and an alcohol extract of *Gynostemma pentaphyllum,* about 10 to about 30 percent by weight of a mixture of an aqueous extract and an alcohol extract of *Camellia sinensis* (green tea), and about 40 to about 75 percent by weight of a mixture of an aqueous extract and an alcohol extract of *Crataegus pinnatifida* (hawthorn berries).

2. The method according to claim 1, further comprising administering to the individual a therapeutically effective amount of one or more anticancer treatments selected from the group consisting of radiation therapy, chemotherapy, surgery, immunotherapy, photodynamic therapy, and a combination thereof.

3. The method according to claim 2, wherein the anticancer treatment comprises chemotherapy.

4. The method according to claim 3, wherein the chemotherapy comprises administering to the individual a therapeutically effective amount of one or more chemotherapeutic drugs.

5. The method according to claim 1, wherein the composition is administered orally to the individual.

6. The method according to claim 1, wherein the composition further comprises a pharmaceutically acceptable carrier.

7. The method according to claim 6, wherein the composition is administered orally to the individual.

8. A method of anticancer therapy comprising administering to an individual at risk of developing a tumor a therapeutically effective amount of a composition comprising about 10 to about 30 percent by weight of a mixture of an aqueous extract and an alcohol extract of *Gynostemma pentaphyllum, about* 10 to about 30 percent by weight of a mixture of an aqueous extract and an alcohol extract of *Camellia sinensis* (green tea), and about 40 to about 75 percent by weight of a mixture of an aqueous extract and an alcohol extract of *Crataegus pinnatifida* (hawthorn berries).

9. The method according to claim 8, wherein the individual is at risk for developing recurrence of tumor.

10. The method according to claim 8, wherein the composition is administered orally to the individual.

11. The method according to claim 8, wherein the composition further comprises a pharmaceutically acceptable carrier.

12. The method according to claim 11, wherein the composition is administered orally to the individual.

* * * * *